(12) United States Patent
Winkelhake

(10) Patent No.: US 7,954,620 B2
(45) Date of Patent: Jun. 7, 2011

(54) PASSENGER CONVEYOR HANDRAIL DRIVE CONTROL STRATEGY

(75) Inventor: Dirk Winkelhake, Bolton, CT (US)

(73) Assignee: Otis Elevator Company, Farmington, CT (US)

( * ) Notice: Subject to any disclaimer, the term of this patent is extended or adjusted under 35 U.S.C. 154(b) by 26 days.

(21) Appl. No.: 12/517,081

(22) PCT Filed: Oct. 9, 2007

(86) PCT No.: PCT/US2007/080750
§ 371 (c)(1),
(2), (4) Date: Jun. 1, 2009

(87) PCT Pub. No.: WO2008/076499
PCT Pub. Date: Jun. 26, 2008

(65) Prior Publication Data
US 2010/0096240 A1    Apr. 22, 2010

(51) Int. Cl.
    *B66B 23/06* (2006.01)
(52) U.S. Cl. .......... 198/331; 198/330
(58) Field of Classification Search .......... 198/323, 198/330, 331, 322
    See application file for complete search history.

(56) References Cited

U.S. PATENT DOCUMENTS

| | | | |
|---|---|---|---|
| 2,221,403 A | 11/1940 | Lindquist et al. | |
| 3,658,166 A * | 4/1972 | Hara et al. | 198/322 |
| 3,677,388 A * | 7/1972 | Boltrek et al. | 198/330 |
| 4,580,675 A * | 4/1986 | Boltrek | 198/331 |
| 5,072,820 A * | 12/1991 | Steffen et al. | 198/323 |
| 5,090,551 A | 2/1992 | Yasuhara et al. | |
| 5,092,446 A | 3/1992 | Sullivan, Jr. et al. | |
| 5,295,567 A | 3/1994 | Zaharia et al. | |
| 5,842,554 A * | 12/1998 | Stoxen et al. | 198/322 |
| 6,161,674 A | 12/2000 | Aulanko et al. | |
| 6,267,219 B1 * | 7/2001 | Spannhake et al. | 198/323 |
| 6,971,497 B2 | 12/2005 | Illedits et al. | |
| 2006/0070846 A1 | 4/2006 | Andreas et al. | |

FOREIGN PATENT DOCUMENTS

| | | |
|---|---|---|
| DE | 19539796 A1 | 4/1997 |
| EP | 0883568 B1 | 10/2002 |
| JP | 2000053353 | 2/2000 |
| JP | 2001139271 | 5/2001 |
| JP | 2001220083 | 8/2001 |

(Continued)

OTHER PUBLICATIONS

International Search Report and Written Opinion of the International Searching Authority for International application No. PCT/US2007/080750 mailed Feb. 11, 2008.

(Continued)

*Primary Examiner* — James R Bidwell
(74) *Attorney, Agent, or Firm* — Carlson, Gaskey & Olds PC

(57) ABSTRACT

A passenger conveyor assembly (20) includes a moveable stepping surface (22). A first drive (50) is operative to move the stepping surface (22). A handrail (30) and a second drive (40) is provided as part of the passenger conveyor assembly (20). A controller (70) controls the second drive (40) independent of the first drive (50) to allow for movement of the stepping surface (22) or the handrail (30) when the other of the handrail (30) or the stepping surface (22) is stationary.

20 Claims, 2 Drawing Sheets

| FOREIGN PATENT DOCUMENTS | | |
|---|---|---|
| WO | 0010902 | 3/2000 |
| WO | 03066500 A1 | 8/2003 |
| WO | 2004035451 A2 | 4/2004 |
| WO | 2005097650 A2 | 10/2005 |

OTHER PUBLICATIONS

International Preliminary Report on Patentability for International application No. PCT/US2007/080750 mailed Mar. 25, 2009.

* cited by examiner

US 7,954,620 B2

PASSENGER CONVEYOR HANDRAIL DRIVE CONTROL STRATEGY

CROSS-REFERENCE TO RELATED APPLICATIONS

This is the U.S. national phase of International Application No. PCT/US07/080,750 filed 9 Oct. 2007 and claims priority to International Application No. PCT/US06/62468 filed 21 Dec. 2006.

BACKGROUND

Passenger conveyors have proven effective for carrying people between different levels within a building or across an elongated pathway, for example. Typical arrangements include a plurality of steps or a belt upon which an individual stands to be carried from one location to another. A handrail typically rides over a balustrade and provides a surface for an individual to grab onto while riding on the conveyor. Typical handrail configurations have a generally flat surface oriented parallel to the direction of movement of the conveyor.

Handrails are driven to move in unison with the steps or moving belt. A handrail drive mechanism causes the desired movement of the handrail. Typical arrangements link a motor responsible for driving the step chain to the handrail drive system. The same motor drives the step chain and the handrail to ensure that the two move in unison. While such arrangements have proven useful, those skilled in the art are always striving to make improvements. One example improvement is shown in the published United States Patent Application 2006/0070846.

For example, it would be useful to simplify the installation and maintenance procedures associated with passenger conveyors. The interconnection between the step chain and handrail drive systems contributes to the complexity and time-consuming nature of such processes. The handrail drive system is a contributor to maintenance and repair requests and it would be useful to provide an improved arrangement to minimize the times a conveyor is unavailable for passenger use.

SUMMARY

An exemplary passenger conveyor assembly includes a moveable stepping surface. A first drive is operative to move the stepping surface in a desired direction. The assembly also includes a handrail and a second drive that is operative to move the handrail. A controller controls the second drive independent of the first drive to allow for movement of the stepping surface or the handrail when the other of the handrail or the stepping surface is stationary.

An exemplary method of controlling operation of a passenger conveyor includes independently controlling movement of a handrail and a stepping surface to allow for movement of the stepping surface or the handrail when the other of the handrail or the stepping surface is stationary.

The various features and advantages of the disclosed examples will become apparent to those skilled in the art from the following detailed description. The drawings that accompany the detailed description can be briefly described as follows.

DETAILED DESCRIPTION

Figure 1:
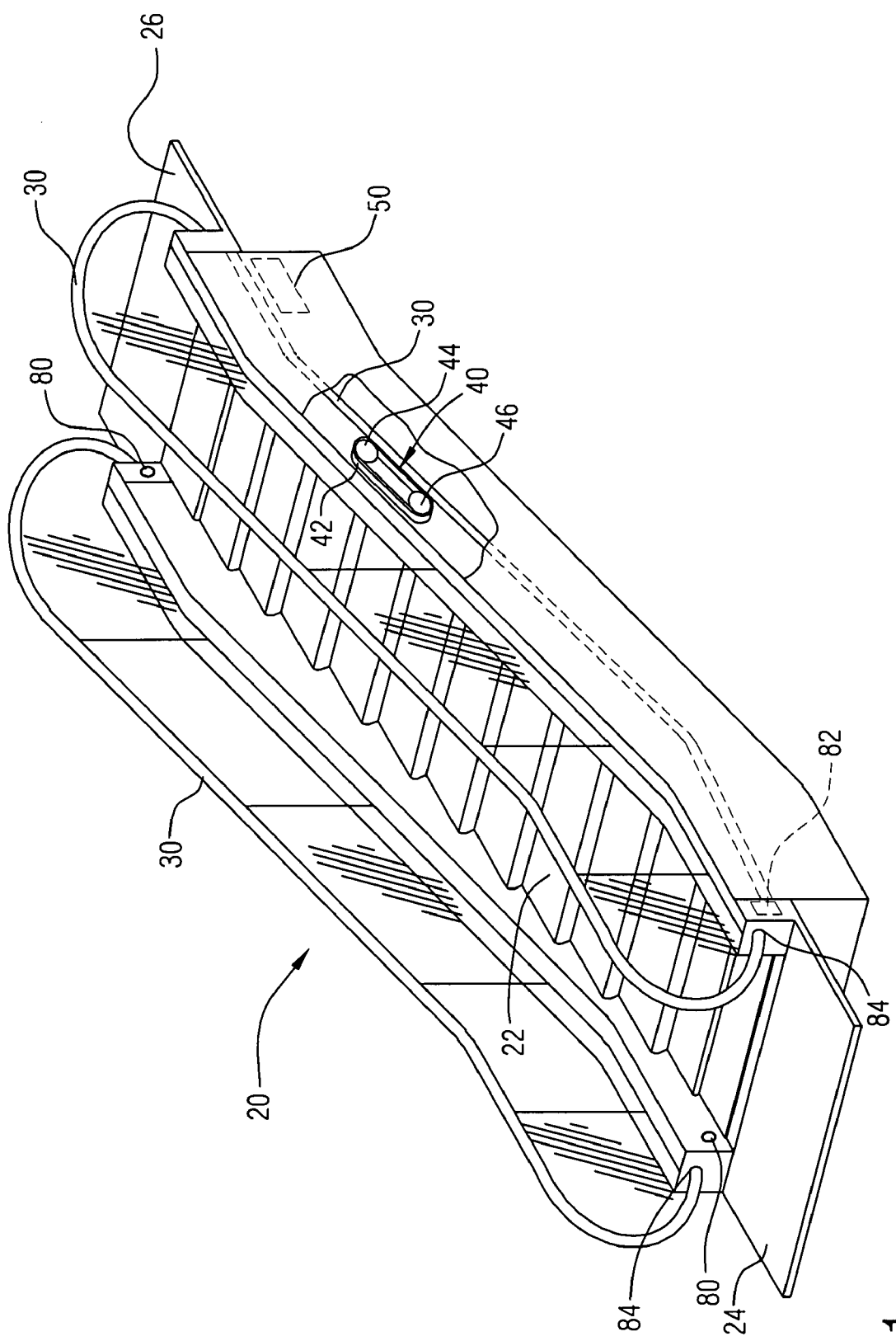
FIG. 1 schematically shows selected portions of an example passenger conveyor including a handrail driving device designed according to an embodiment of this invention.

FIG. 1 schematically shows a passenger conveyor 20. In this example, the passenger conveyor is an escalator having a plurality of steps 22 for carrying passengers between landings 24 and 26 at different levels within a building. The plurality of steps 22 is one example type of moveable stepping surface. This invention is not limited to escalators but is also applicable to other forms of passenger conveyors such as moving walkways, for example. Other conveyors may have other stepping surfaces such as treadplates or belts. The steps 22 will be used as an example for discussion purposes.

The example passenger conveyor of FIG. 1 includes a handrail 30 that moves along with the steps 22. A handrail drive device 40 includes a drive member 42 that engages the handrail 30 to propel the handrail 30 in a desired direction. The example handrail drive device 40 includes a motor 44 that is dedicated to moving the handrail 30. The motor 44 is associated with a wheel at one end of a loop followed by the drive member 42, which comprises a belt in this example. Another wheel 46 is at an opposite end of the loop. The motor 44 causes the drive member 42 to rotate about the loop, which drives the handrail 30 as desired because of engagement between the handrail 30 and the drive member 42.

The handrail drive device 40 is distinct from a drive assembly 50 used to propel the steps 22 by driving a step chain (not illustrated). The motor 44 is distinct from a motor of the drive assembly 50. Accordingly, the illustrated arrangement is different than traditional passenger conveyor systems where the handrail was driven by the same motor used to move the step chain. In another example, the separate control aspects are accomplished using a common motor for the steps and handrail but a distinct and separately controllable clutch type mechanism couples the handrail drive with the motor.

Figure 2:
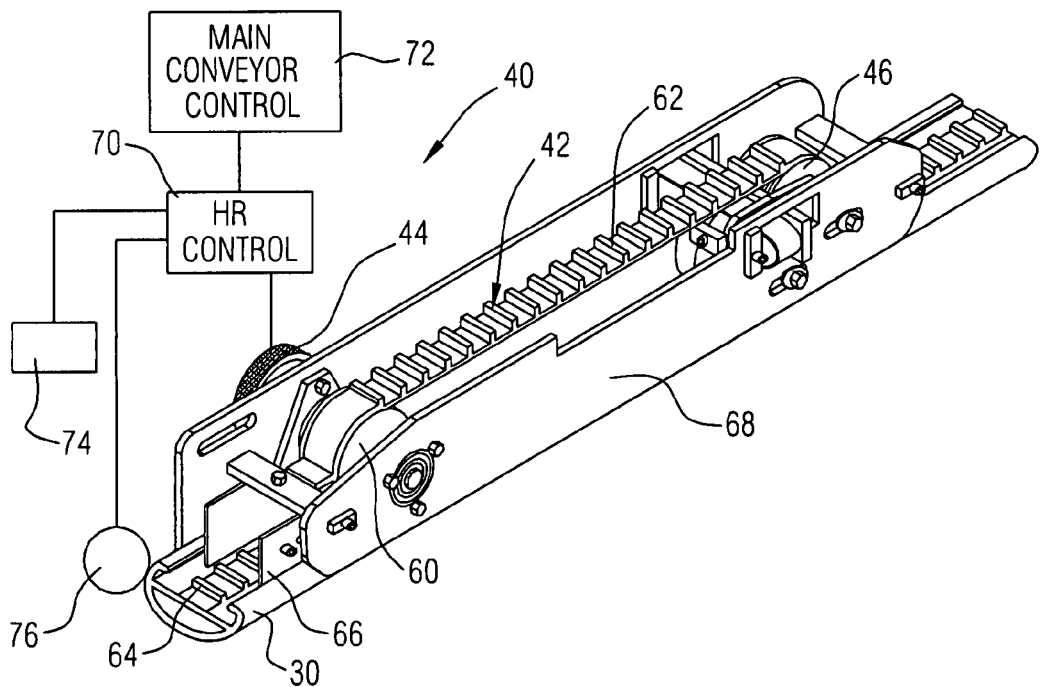
FIG. 2 schematically shows an example drive device.

FIG. 2 schematically shows one example handrail drive device 40. In this example, the motor 44 comprises a permanent magnet motor. One feature associated with using a permanent magnet motor is that relatively large torques required to drive a handrail can be achieved with a relatively small sized motor. Another feature of a permanent magnet motor is that it allows for closely controlling the speed at which the motor 44 moves the drive member 42. Other types of motors could also be used, such as conventional induction motors.

This example drive member 42 comprises a toothed belt that follows a loop around the wheel 46 and a wheel 60 that can be considered a drive sheave because it is driven by the motor 44. The toothed belt drive member 42 has teeth 62 that are configured to engage correspondingly configured teeth 64 on the handrail 30. A guiding support 66 maintains the corresponding portion of the handrail 30 in a position to ensure desired engagement between the teeth 62 and 64. As the motor 44 rotates the wheel 60, the drive member 42 moves and causes a desired movement of the handrail 30. A mounting structure 68 facilitates securing the device 40 in a desired position on a conveyor truss or other support structure.

The illustrated example includes a handrail drive controller 70 that controls operation of the motor 44 to ensure that the handrail is moving when needed and at a desired speed that is coordinated with movement of the steps 22. The handrail drive controller 70 communicates with a main conveyor controller 72, which is responsible for controlling the drive assembly 50. The main conveyor controller 72 provides information to the handrail drive controller 70 regarding the speed and direction of movement of the steps 22 so that the handrail drive controller 70 can control the motor 44 to achieve a corresponding handrail movement.

In one example a connection between the main conveyor controller 72 and the handrail drive controller 70 operates as a power supply to the handrail drive device 40. For example, whenever the main conveyor controller 72 determines that the conveyor is stopped or out of service, it controls whether power is supplied to the handrail drive device according to preset criteria.

The example handrail drive controller 70 also receives information from a step chain sensor 74 that indicates a speed of movement of the step chain and the steps 22. One example includes at least one proximity sensor arranged to detect movement of pins associated with rollers of the steps or step chain to provide an indication of a speed of movement. A handrail speed sensor 76 provides an indication of actual handrail speed. Given this description, those skilled in the art will be able to select from commercially available sensors to realize an arrangement that meets their particular needs. The handrail drive controller 70 uses such sensor information and knowledge regarding the operating characteristics of the motor 44 to customize the operation of the motor 44 to ensure that the handrail 30 is moving at a speed that is appropriate for a current speed of step movement. In one example, the handrail drive controller 70 comprises a variable frequency controller, which allows for customizable speed control of the motor 44.

In the illustration, the handrail drive controller 70 and the main conveyor controller 72 are schematically shown separately for discussion purposes. In one example, each comprises a separate controller device. In another example, a single controller performs the functions of the handrail drive controller 70 and the main conveyor controller 72.

In some examples, separate motors 44 and handrail drive devices 40 are provided for each handrail, respectively (e.g., one of the right and another of the left of the stepping surface). In such an embodiment, it is possible to independently control each handrail (e.g., each side by controlling the motors 44 separately, in another example, a single motor 44 provides the force needed to move the drive devices 40 associated with the handrail on each side of the conveyor.

Controlling the handrail drive device 40 independently of the drive assembly 50 allows for additional features that are not possible in an arrangement where the handrail is directly driven by the same device that drives the steps. The example handrail drive controller 70 controls the handrail drive 40 independent of the step drive assembly 50 to allow for movement of the plurality of steps 22 or the handrail 30 when the other of the handrail 30 or the plurality of steps 22 is stationary. The handrail drive controller 70 in one example controls the handrail drive 40 to stop the handrail 30 responsive to a selected condition in which the plurality of steps 22 continue to move for at least some time after the handrail 30 has stopped.

In one example, the handrail drive controller 70 causes the handrail drive 40 to stop moving the handrail 30 in the event that the passenger conveyor 20 is idle when no passengers are being carried by the steps 22. Referring again to FIG. 1, at least one sensor 80 is associated with the conveyor assembly 20 for detecting when at least one passenger is in the vicinity of the steps 22 or on at least one of the steps 22. In the illustrated example, light-based sensors 80 are positioned near each of the landings 24 and 26 for detecting when at least one passenger is present at a landing or in the space within which the passenger can be carried by the steps 22. One example includes known light-based sensors for detecting when an individual passes one of the sensors.

Whenever the passenger conveyor assembly 20 is idle and no passengers are present, the handrail drive controller 70 stops the handrail drive 40 so that the handrail 30 does not move. At the same time, the main conveyor controller 72 continues to cause the drive assembly 50 to operate such that the steps 22 continue moving. Given that handrail movement accounts for a significant portion of energy consumption with many passenger conveyor systems, the ability to individually control the handrail during such idle conditions allows for significant energy savings by stopping the handrail 30 from moving while allowing the plurality of steps 22 to continue moving.

One feature of this example is that the moving steps or treads gives the approaching passenger a visual indication that the conveyor is operational, whereas the non-moving handrail, which is typically a uniform color, provides less visual indication and likely will not be noticed.

Another feature is improved maintenance and life of the handrail drive since it is not being continuously operated. Also, during repair or testing, the handrail drives could be separately tested without the need to start up the entire escalator system.

In one example, whenever a passenger is detected as approaching or contacting a landing or at least one of the steps 22, the handrail drive controller 70 causes the handrail drive 40 to operate to accelerate the handrail 30 up to a speed where the handrail moves in conjunction with the plurality of steps 22.

Another condition in which it is desirable to stop the handrail 30 even though the steps 22 continue moving includes a situation where a switch is activated that provides an indication of a desire to stop movement of the conveyor assembly 20. Referring to FIG. 1, a switch 82 is associated with a handrail entry 84. The switch 82 operates in a known manner to provide an indication of when an object enters an opening of the handrail entry 84 such that the object may become caught between the structure of the balustrade of the passenger conveyor assembly and the handrail 30, for example. As known, activation of such switches results in turning off the conveyor to avoid entrapment of such an object under such conditions. With the illustrated example, the handrail drive controller 70 causes the handrail drive 40 to stop the handrail 30 immediately responsive to activation of the switch 82. This allows for the handrail 30 to stop before the steps 22 are able to stop.

Even though the main conveyor controller 72 controls the drive assembly 50 to stop moving the steps 22 in immediate response to activation of the switch 82, it is not possible for the steps 22 to stop as fast as the handrail 30 can stop. The steps 22 must continue to move even after a stop command is issued to avoid a rapid deceleration rate that would result in causing a passenger on one of the steps to fall. Additionally, the weight of the step band makes it difficult to achieve an absolute stop immediately in response to activation of the switch 82. Stopping movement of the handrail 30 before being able to bring the steps to a complete stop is possible, however, and provides enhanced prevention of object entrapment at the handrail entry 84 even though the steps 22 continue moving for a short time after activation of the switch 82. Without the independent control of the handrail movement, the handrail 30 would continue moving with the steps 22 for a distance that is at least 250 mm in some examples. In the illustrated example, the handrail 30 can stop almost immediately responsive to activation of the switch 82 even though the steps continue moving. In other words, the handrail 30 stops before the steps 22 stop moving.

Those skilled in the art who have the benefit of this description will be able to program a controller to perform in a manner that meets the requirements of their particular installation.

Figure 3:
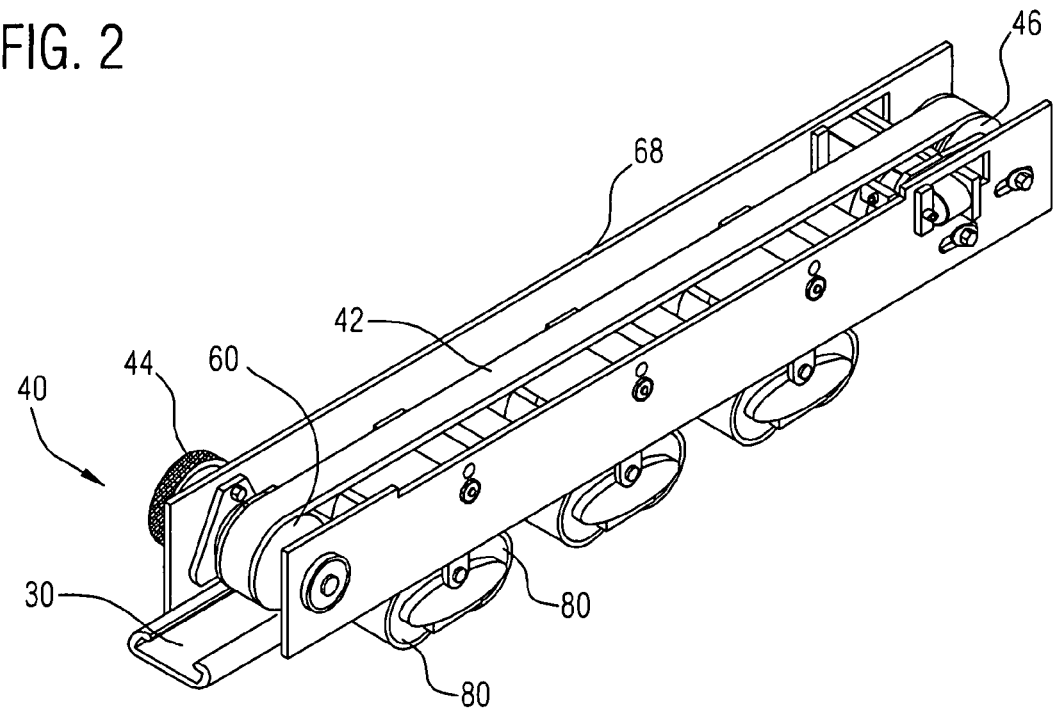
FIG. 3 schematically shows selected portions of another example drive device.

FIG. 3 shows another example handrail drive device. In this example, the drive member 42 and the handrail 30 are configured differently compared to the example of FIG. 2. In this example, the more traditional flat drive belt and handrail configurations are used. The flat belt drive member 42 in this example relies upon a frictional engagement with the handrail 30. Rollers 80 engage one side of the handrail to ensure a proper driving engagement between the handrail 30 and the drive member 42. Otherwise, the example of FIG. 3 operates like the example of FIG. 2.

Another example (not shown) includes conventionally configured handrail drive wheels in place of the flat belt drive member 42.

One feature of the disclosed examples is that the handrail drive device 40 can be located anywhere within a passenger conveyor system that is convenient for an installer provided that the structure 68 can be adequately supported in a position to provide proper engagement between the drive member 42 and the handrail 30. This not only simplifies installation but provides advantages for maintenance or repair as the handrail drive device can be located more conveniently. When the handrail drive device is located remotely from the step chain drive assembly, each drive can be serviced without any interference from the other.

Another feature is that a handrail drive device 40 can be retrofit into an existing conveyor system. The coupling between the step chain drive and the handrail drive can be disconnected or otherwise disabled and the handrail drive device 40 can be inserted in its place. This allows for a wider range of choice in replacement handrails, for example, as different handrail configurations can be accommodated by a correspondingly configured handrail drive device 40. For example, it may be possible to insert a positive drive handrail (having drive teeth) in place of a friction-based driven handrail by introducing a handrail drive device 40 as shown in FIG. 2. Such a change is not possible with a conventional arrangement that is configured for only one type of handrail.

Another feature of the disclosed examples is that the handrail operation is smoother compared to an arrangement where the handrail is driven by the same motor used to drive the step chain. The dedicated motor of the example devices provides a smoother transmission of driving force to the handrail and avoids the vibrations associated with some movements of a step chain.

Additionally, in some examples, separating the handrail drive motor from a step chain motor reduces the complexity of each drive arrangement because it allows for addressing the needs of only one of the two instead of both, reduces wear, facilitates less maintenance and reduces the likelihood of a need for repair.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. A passenger conveyor assembly, comprising:
a moveable stepping surface;
a first drive that is operative to move the stepping surface;
a handrail;
a second drive that is operative to move the handrail, the second drive comprising a motor that is dedicated to moving only the handrail; and
a controller that controls the second drive independent of the first drive to allow for movement of the stepping surface or the handrail when the other of the handrail or the stepping surface is stationary.

2. The assembly of claim 1, wherein the controller controls the second drive to stop the handrail responsive to a selected condition in which the stepping surface continues to move at least some time after the handrail has stopped.

3. The assembly of claim 2, wherein the selected condition includes no passengers on the stepping surface.

4. The assembly of claim 3, wherein the stepping surface continues to move responsive to the selected condition.

5. The assembly of claim 3, comprising
a sensor that provides an indication of whether at least one passenger is at least within a vicinity of the stepping surface; and
wherein the controller receives the indication from the sensor.

6. The assembly of claim 2, wherein the selected condition includes activation of a switch that indicates a desire to stop at least one of the stepping surface or the handrail.

7. The assembly of claim 6, wherein the handrail stops before the stepping surface stops.

8. The assembly of claim 6, wherein the switch comprises a safety switch near a handrail entry.

9. The assembly of claim 8, wherein the controller controls the second drive and the first drive to stop simultaneously responsive to the activation of the switch and the handrail stops before the stepping surface stops.

10. A method of controlling operation of a passenger conveyor comprising a moveable stepping surface and a handrail, the method comprising:
independently controlling movement of the handrail and the stepping surface to allow for movement of the stepping surface or the handrail when the other of the handrail or the stepping surface is stationary, the movement of the handrail occurring responsive to operation of a motor that is dedicated to moving only the handrail.

11. The method of claim 10, comprising
stopping the handrail responsive to a selected condition in which the stepping surface continues to move at least some time after the handrail has stopped.

12. The method of claim 11, wherein the selected condition includes no passengers on the stepping surface.

13. The method of claim 12,
comprising continuing to move the stepping surface responsive to the selected condition.

14. The method of claim 12, comprising
determining whether at least one passenger is at least within a vicinity of the stepping surface.

15. The method of claim 11, wherein the selected condition includes activation of a switch that indicates a desire to stop at least one of the stepping surface or the handrail.

16. The method of claim 15, comprising
stopping the handrail before the stepping surface stops.

17. The method of claim 15, wherein the switch comprises a safety switch near a handrail entry.

18. The method of claim 17, comprising
simultaneously initiating a stop of the handrail and the stepping surface and wherein the handrail stops before the stepping surface stops.

19. A passenger conveyor assembly, comprising
a moveable stepping surface;
a first drive that is operative to move the stepping surface;
a handrail;
a second drive that is operative to move the handrail; and a controller that controls the second drive independent of the first drive to
  (i) stop the handrail while allowing the stepping surface to continue moving when there are no passengers on the stepping surface; or
  (ii) stop the handrail sooner than the stepping surface responsive to a switch activation that indicates a need to stop at least one of the handrail or the stepping surface.

20. The assembly of claim 19, comprising a handrail entry at a location where the handrail enters another portion of the conveyor assembly and wherein the switch activation indicates that an object is undesirably entering the handrail entry.

* * * * *